US005784160A

United States Patent [19]

Naqwi

[11] Patent Number: 5,784,160
[45] Date of Patent: Jul. 21, 1998

[54] NON-CONTACT INTERFEROMETRIC SIZING OF STOCHASTIC PARTICLES

[75] Inventor: Amir A. Naqwi, Shoreview, Minn.

[73] Assignee: TSI Corporation, St. Paul, Minn.

[21] Appl. No.: 541,577

[22] Filed: Oct. 10, 1995

[51] Int. Cl.$^6$ ............................................. G01B 9/02
[52] U.S. Cl. ........................ 356/345; 356/336; 356/349; 356/357
[58] Field of Search ............................. 356/336, 345, 356/357, 361, 349

[56] References Cited

U.S. PATENT DOCUMENTS

| | | |
|---|---|---|
| 3,915,572 | 10/1975 | Orloff . |
| 3,953,128 | 4/1976 | Holly . |
| 4,948,257 | 8/1990 | Kaufman et al. . |
| 4,986,659 | 1/1991 | Bachalo . |
| 5,432,605 | 7/1995 | Naqwi . |
| 5,453,837 | 9/1995 | Naqwi et al. ............................ 356/345 |
| 5,513,004 | 4/1996 | Naqwi et al. . |

FOREIGN PATENT DOCUMENTS 24 48 651  10/1974  Germany .

*Primary Examiner*—Frank G. Font
*Assistant Examiner*—Robert Kim
*Attorney, Agent, or Firm*—Frederick W. Niebuhr

[57] ABSTRACT

A device and process for interferometric sizing of stochastic (irregular and/or inhomogeneous) particles is disclosed. The device generates a pair of laser beams that interfere with one another to form a measuring volume including interference fringes. Particles crossing the fringes scatter light collected by two or more optical receivers. Outputs of the optical receivers are provided to signal processing and phase processing circuits, to generate indications of particle velocities based on signal frequencies, and indications of particle sizes based on phase shift values. Particles are characterized as to size by generating probability density functions of phase, based on multiple particle traverses through the measuring region, thus to more accurately measure groups of particles, despite the lack of reliability inherent in measuring a single particle. The device is operable in a calibration mode, using particles of known sizes or size distributions. In the calibration mode, phase processing circuitry uses the known particle size distributions and the measured phase distributions to determine certain coefficients which are stored in the phase processing circuitry. These coefficients are later used to generate size distribution functions, based on phase distribution functions obtained by measuring multiple phase values generated by stochastic particles of unknown size.

29 Claims, 10 Drawing Sheets

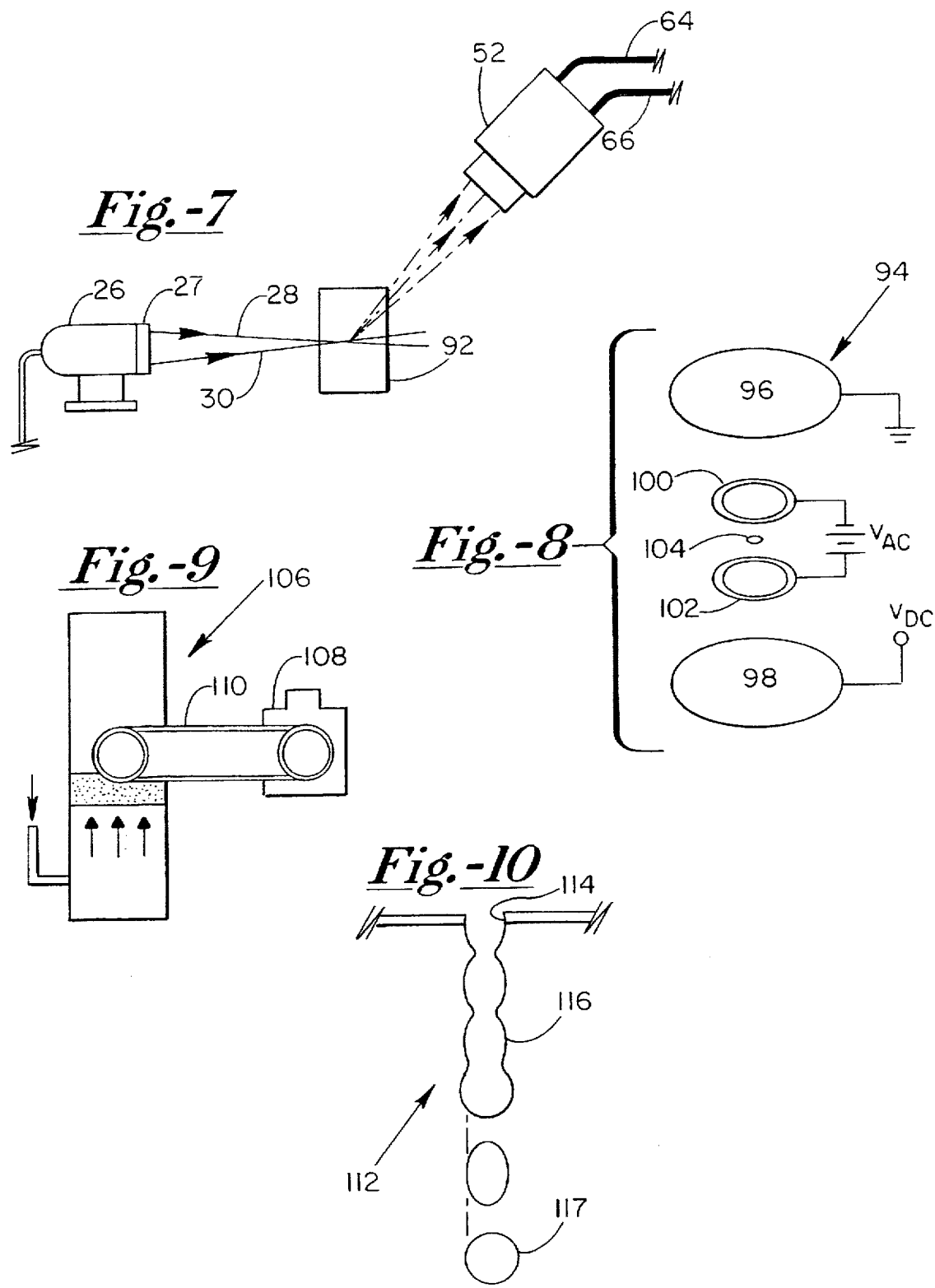

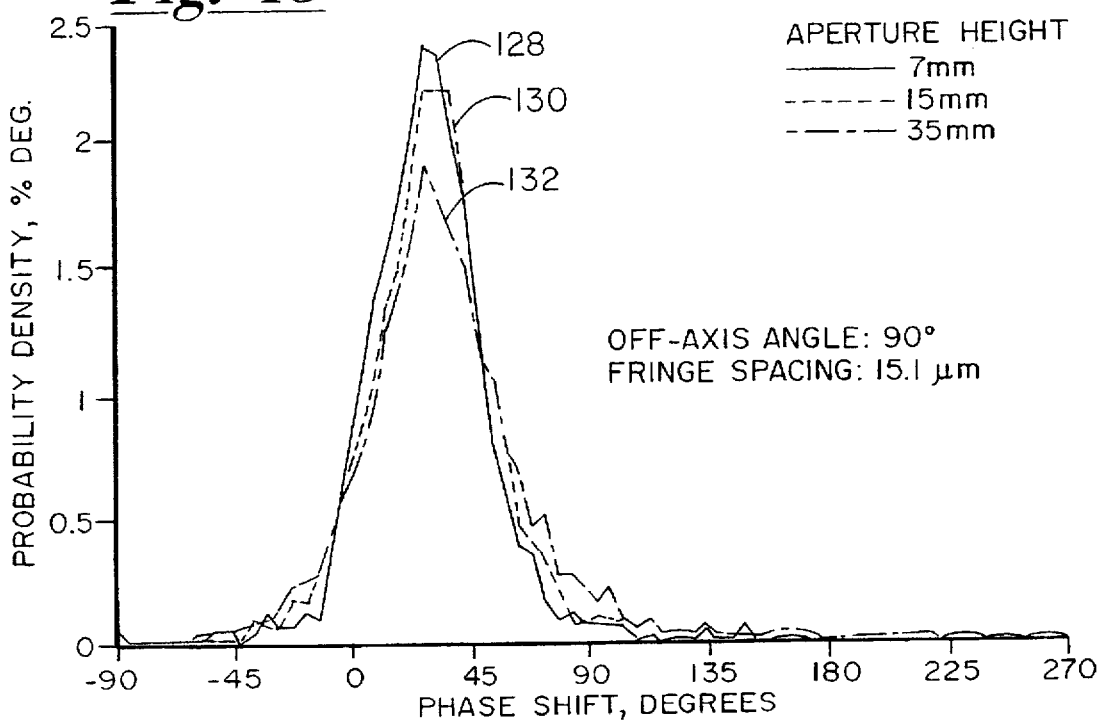
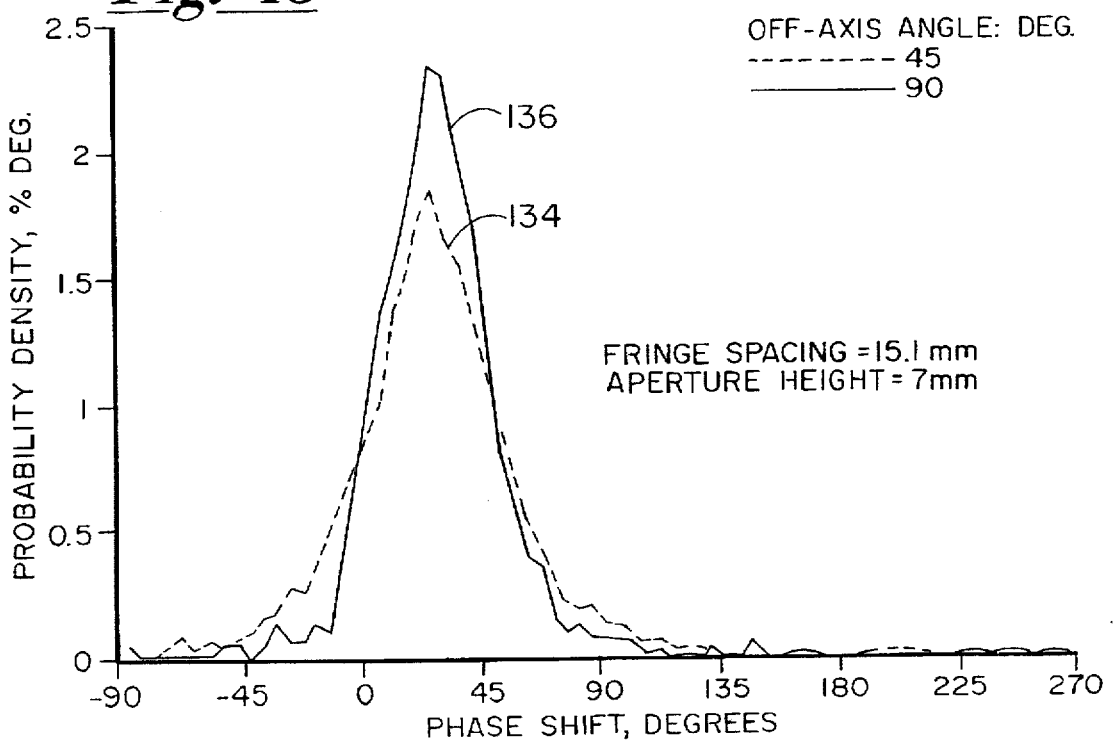

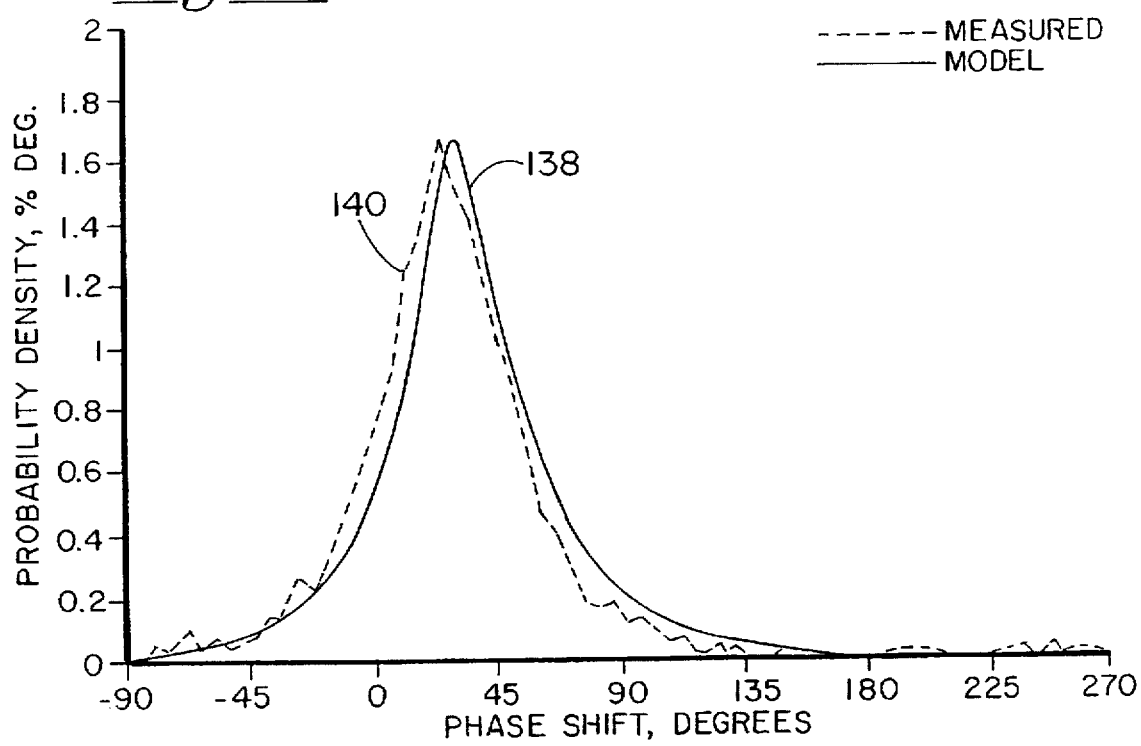

NON-CONTACT INTERFEROMETRIC SIZING OF STOCHASTIC PARTICLES

BACKGROUND OF THE INVENTION

The present invention relates to instrumentation for non-contact measurement of particles to determine size and other characteristics, and more particularly to the processing of electrical signals in such instrumentation to enhance characterization of stochastic particles. As used herein, the phrase "stochastic particles" refers to particles with an irregular shape, a non-homogeneous composition or both.

Optical systems are used frequently in the study of two-phase or multiple phase flows. Measurements are non-contact and do not disrupt or otherwise interfere with the flows. Measurements can be made in situ, to yield real time information exhibiting high spatial and temporal resolution.

One approach, known as the phase Doppler technique, involves causing two beams of laser or other coherent energy to intersect and form interference fringes throughout a measuring region. The measuring region is positioned within a two-phase flow and flow movement causes particles, bubbles or other elements in the flow to traverse the measuring region and scatter light. The scattered light is detected at two or more locations to establish a difference in phase. The phase difference is used as an indication of particle size. Users prefer the phase Doppler approach, because the phase measurements are more reliable than other characteristics of the scattered light, e.g. scattered power or visibility of a fluctuating signal.

To date, the phase Doppler technique has been employed primarily for measuring spherical particles, which tend to be consistent in their scattering of coherent energy, regardless of their orientation. Non-spherical but regular particles tend to exhibit symmetrical light scattering patterns that provide information about local radii of curvature. Non-spherical objects with uniform radii of curvature also can be measured. A device for sizing cylindrical objects such as optical fibers is disclosed in U.S. Pat. No. 5,432,605, issued Jul. 11, 1995 and assigned to the assignee of this application.

The above success notwithstanding, conventional phase Doppler techniques are not well suited for characterizing stochastic particles. Irregular and nonhomogeneous particles scatter coherent energy in patterns that vary with changes in particle orientation. Such particles cannot be represented by equivalent spheres, nor is the concept of local radius of curvature useful in describing such particles. Measurements of spatial symmetry enable discrimination among such particles, but yield no useful particle size information.

There is a need for determining the sizes of stochastic particles in two-phase or multiphase environments. For example, multiphase flows with irregular elements occur in coal combusters and in slurry transport devices. Textured paint incorporating particles of metal or other solids and non-homogenized milk yield droplets that may be uniform in size and shape, yet of non-homogeneous composition.

Therefore, it is an object of the present invention to provide an interferometric system for measuring and characterizing stochastic particles, based on phase information generated as the particles scatter coherent energy.

Another object is to provide a signal processing means for receiving signals generated in response to detection of coherent energy scattered by stochastic particles and for generating reliable particle size information based on phase differences of the signals.

A further object is to provide a means for accumulating phase difference information based on multiple individual particle traverses through a measuring region defined by intersecting beams of coherent energy, and for generating a frequency distribution of particle sizes based on the accumulated phase information.

Yet another object is to provide a means, within a particle characterizing system, for calibrating components of the system used to convert signal phase information into particle size information.

SUMMARY OF THE INVENTION

To achieve these and other objects, there is provided an apparatus for non-contact measuring of light scattering elements. The apparatus includes an illumination means for selectively directing coherent energy onto a medium, to define a measuring region traversed by light scattering elements contained in the medium as the medium moves relative to the measuring region. An energy detecting means is provided for sensing the coherent energy scattered by each one of the light scattering elements as that element traverses the measuring region. The detecting means senses the scattered coherent energy at first and second locations spaced apart from the measuring region and generates first and second signals based on the coherent energy sensed at the first and second locations, respectively.

A signal processing means is operatively coupled to the energy detecting means to receive the first and second signals. The signal processing means generates a phase value representing a temporal shift between the first and second signals. A collection means is provided for accumulating multiple phase values corresponding to multiple scattering element traverses through the measuring region. The collection means generates phase information based on the accumulated phase values. A conversion means generates element characterizing information based on said phase information.

Typically the light scattering elements are particles and the medium is a fluid. The phase information can comprise a frequency distribution of the accumulated phase values, with the element characterizing information comprising a frequency distribution of particle size values. The element information also can include an indication of particle irregularity, i.e. the extent to which the particles are nonhomogeneous, nonspherical, or both.

The preferred illumination means generates two linearly propagating coherent energy beams that interfere with one another at their intersection to form interference fringes across the measuring region. Fluctuations in scattered energy as the particle or other scattering element traverses the measuring region provide a measure of velocity in the direction perpendicular to the interference fringes. To provide direction as well as velocity information, one of the beams can be shifted in its frequency, causing the set of interference fringes to propagate across the measuring region. If desired, the illumination means can include two further pairs of coherent energy beams, with the beam pairs positioned relative to each other to sense velocity in three mutually perpendicular directions.

Normally, the multiple scattering element traverses that generate phase information comprise single traverses by multiple scattering elements. As an alternative, the multiple traverses can consist of multiple, repeated traverses of a single particle through the measuring volume. This latter approach can be used to generate a frequency distribution of particle sizes for a single particle and is useful in calibrating the apparatus.

The phase information produced by the signal processing means can take the form of a histogram or frequency distribution over a range of phase difference values. As an alternative, this information may consist of a mean phase value and a standard deviation of phase, of a frequency distribution of phase values, in which case the information is combined with a monosize distribution function (advantageously a double exponential function) for generating the measurement information.

Thus in accordance with the present invention, particles and other light scattering elements can be reliably measured as to their size and other characteristics, despite the fact that the light scattering elements individually may scatter light at widely varying intensities, depending principally upon their orientation. When considered in sets or ensembles of multiple measuring region traverses, stochastic light scattering elements exhibit a surprisingly high degree of order and simplicity, leading to a reliable and useful means of measuring size distributions of the scattering element sets, despite the lack of predictability of measuring an irregular light scattering element individually. The result is a more reliable characterization of stochastic light scattering elements.

IN THE DRAWINGS

For a further understanding of the above and other features and advantages, reference is made to the following detailed description and to the drawings, in which:

FIG. 7 is a partial view of the system in FIG. 1, in a calibration mode employing a calibration device;

FIGS. 8, 9 and 10 illustrate alternative calibration devices;

Figure 11:
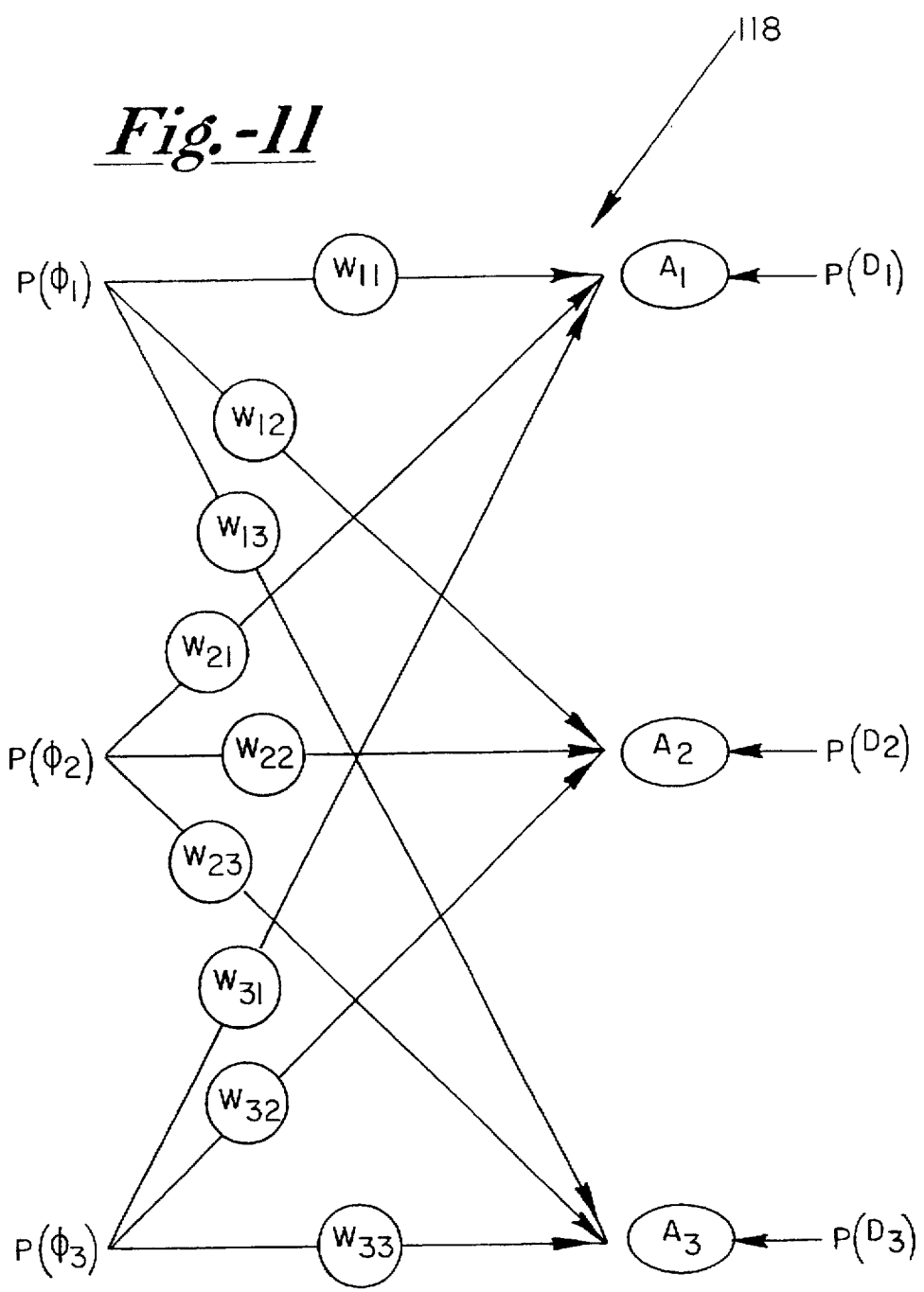
Figure 12:
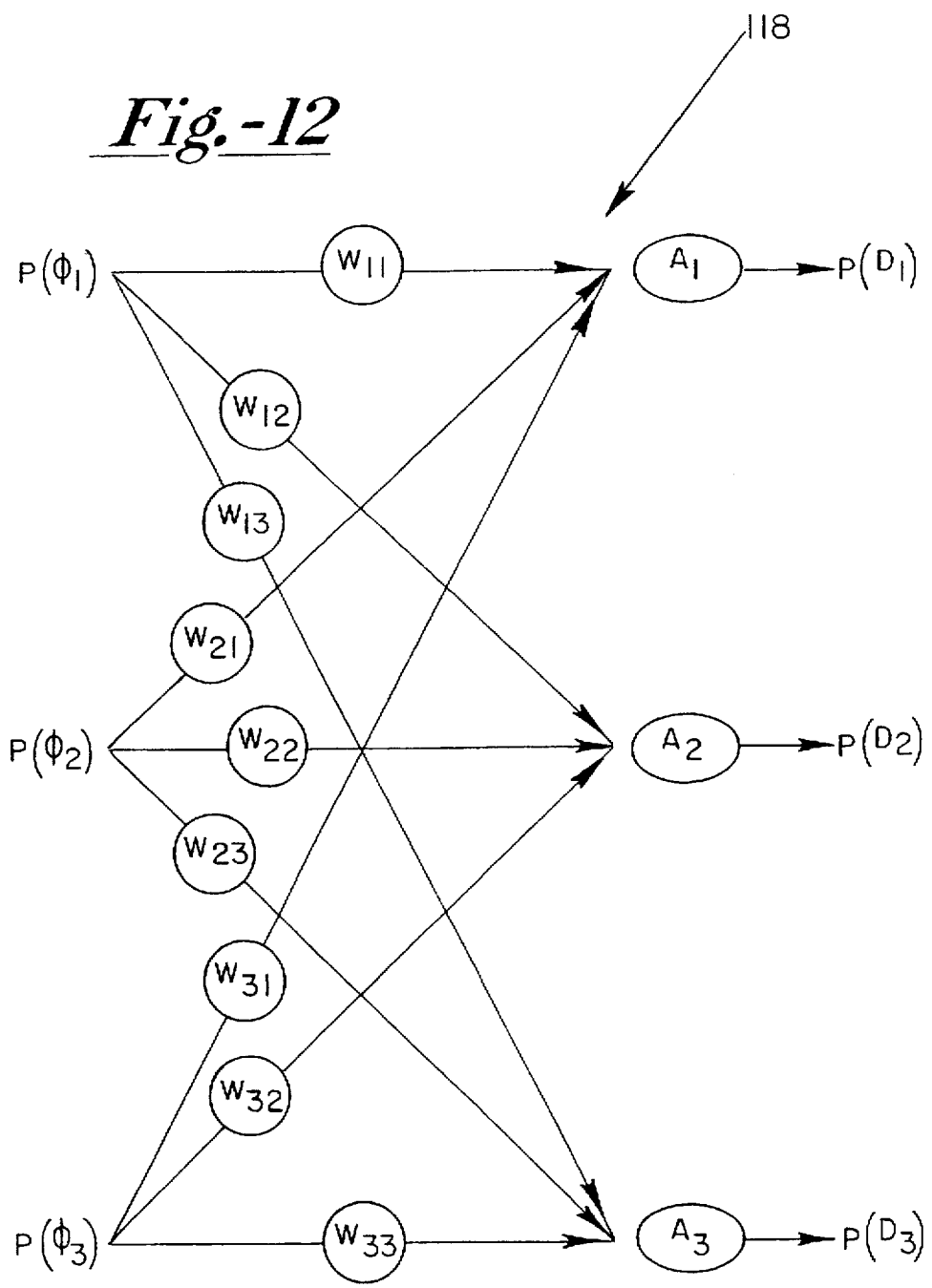
Figure 13:
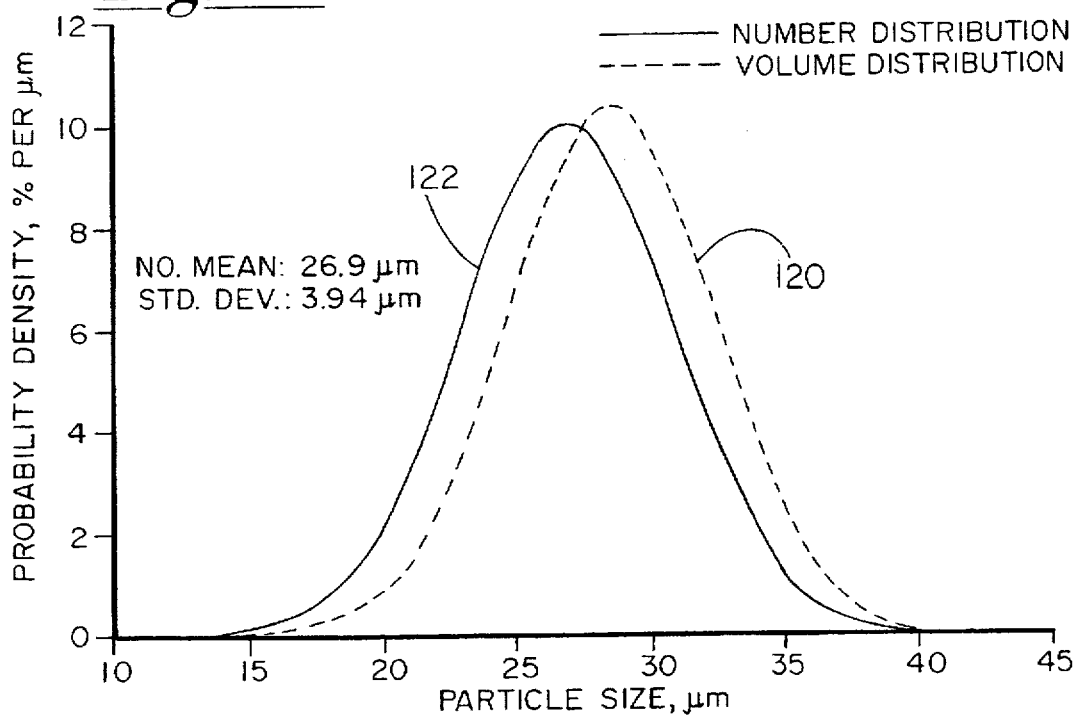
Figure 14:
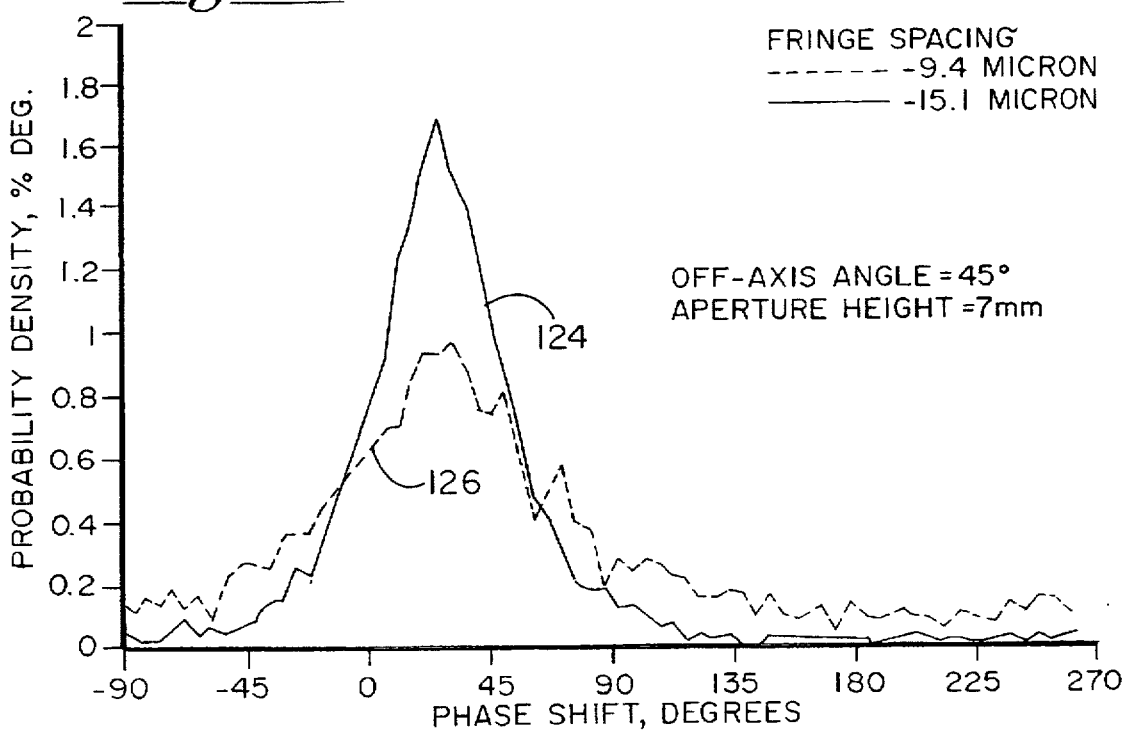
Figure 18:
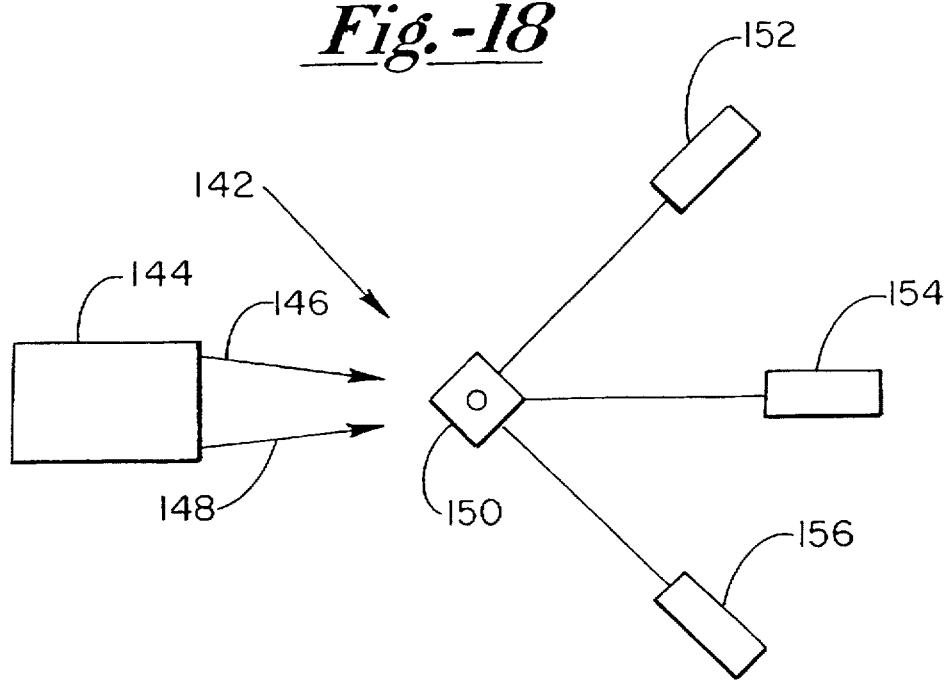
Figure 19:
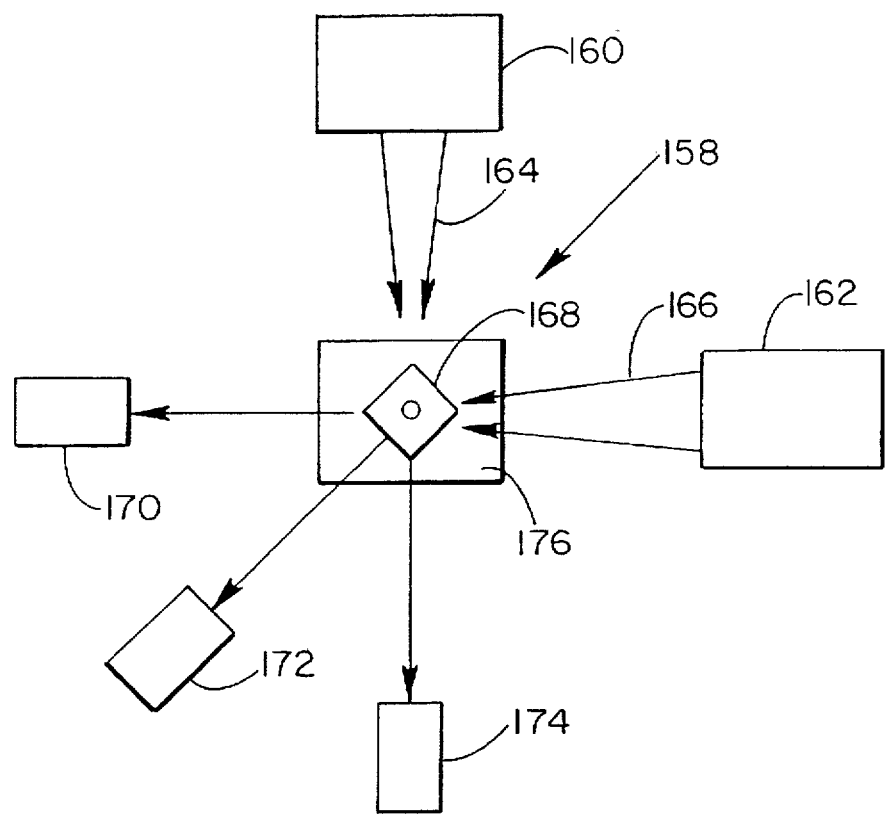
Figure 20:
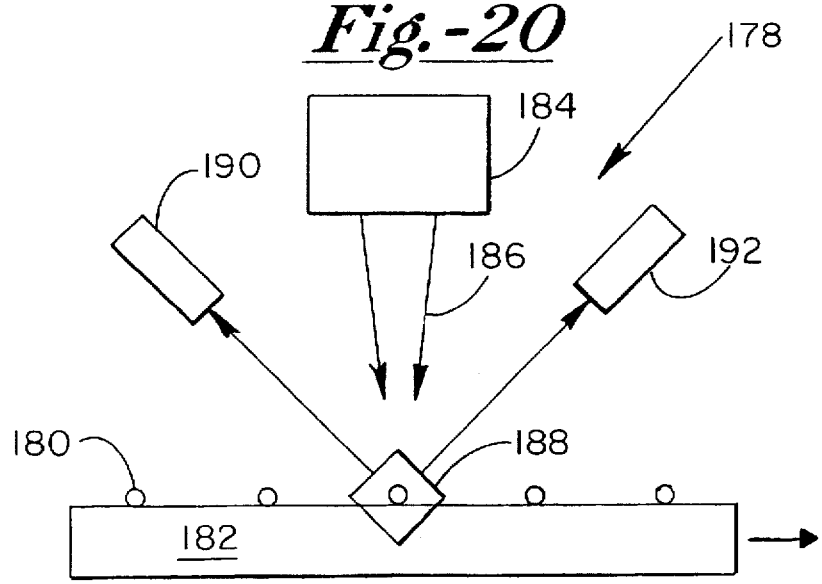

FIGS. 11 and 12 schematically illustrate a neural network employed in a conversion device of the system;

FIG. 13 illustrates frequency distributions of particle size, as used in calibrating the system;

FIGS. 14, 15 and 16 illustrate frequency distributions of phase, obtained by using the system to monitor two-phase flows;

FIG. 17 is a chart comparing a measured phase distribution with a phase distribution predicted using a double exponential model;

FIG. 18 illustrates an alternative particle measuring system employing three detectors for sensing scattered light;

FIG. 19 illustrates another embodiment particle measuring system employing three pairs of coherent energy beams to obtain three-dimensional size and velocity information; and FIG. 20 is a schematic view of a further alternative particle measuring system for measuring particles based primarily on light reflected by the particles supported on a solid medium.

DETAILED DESCRIPTION OF THE PREFERRED EMBODIMENTS

Figure 1:
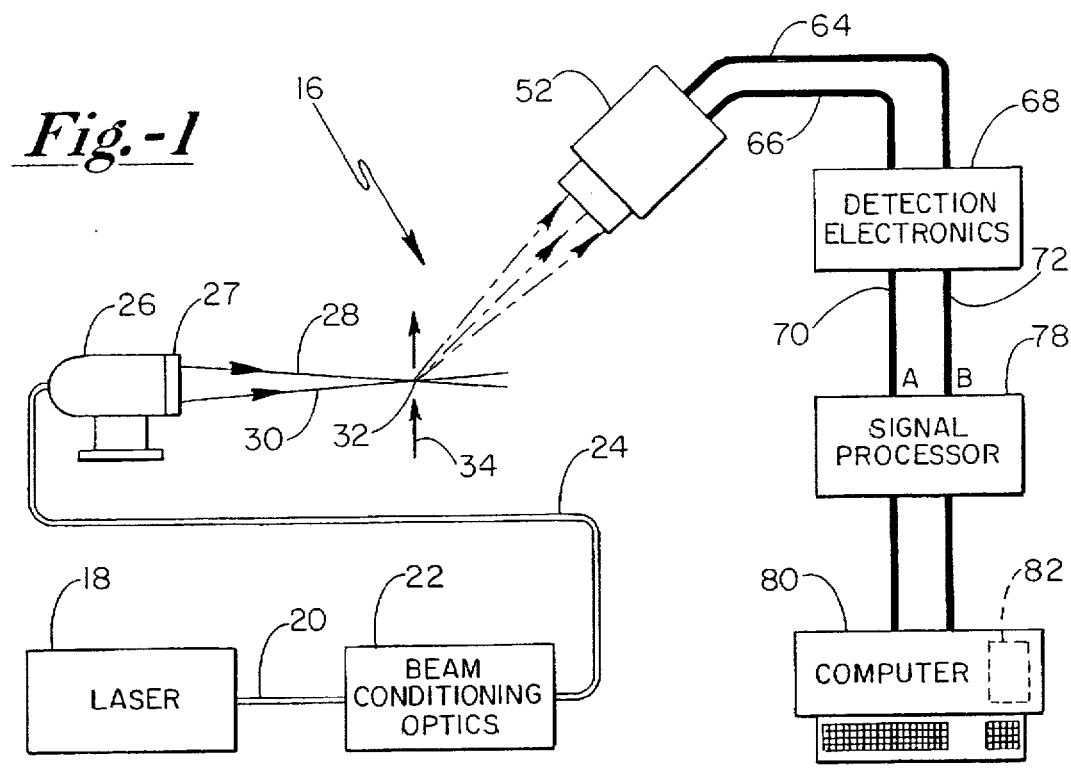
FIG. 1 is schematic view of a system for sizing stochastic particles, constructed in accordance with the present invention.

Turning now to the drawings, there is shown in FIG. 1 an interferometric system 16 for sizing particles and other light scattering elements. The system includes a laser head 18 that includes a diode laser and collimating optics (not shown) for generating a collimated laser beam 20. The laser beam is received by beam conditioning optics 22 that include a beam splitter (not shown) that produces a pair of collimated laser beams responsive to receiving beam 20. One of the collimated beams is shifted in frequency (typically by 40 MHZ) relative to the other beam, by directing it through an accoustal-optic modulator. Accordingly, the beam conditioning optics generate two collimated laser beams that differ in frequency by a predetermined amount.

Optical fibers 24 carry the laser beams to a transmitting device 26, where the fiber optic cable output is directed through a focusing lens 27 to produce two collimated laser beams 28 and 30 that converge upon and are focused at a measuring region 32, i.e. the volume over which the two beams intersect.

Transmitting device 26 is operated to position the measuring region within a two-phase flow 34 that includes particles or other light scattering elements and a medium in which the particles are supported. For example, the flow can consist of aluminum oxide particles 36 such as those shown in FIGS. 3 and 4, carried by air or another gaseous medium.

Figure 3:
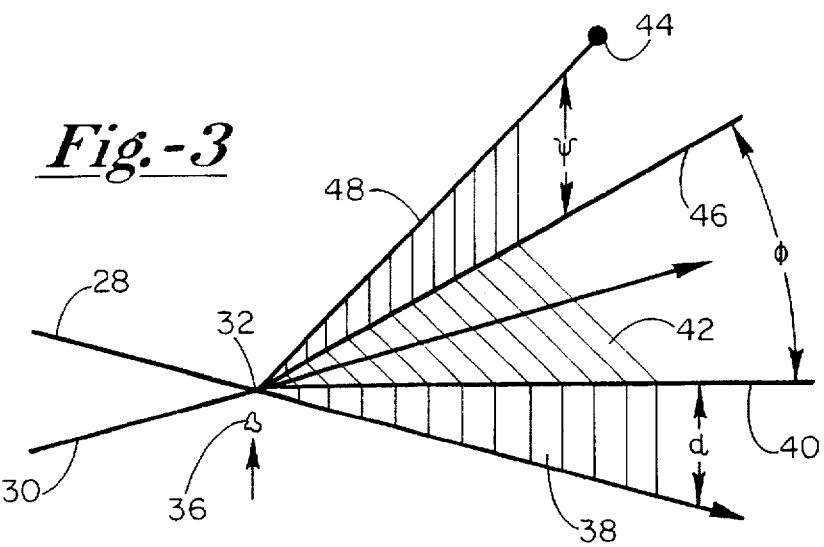
FIG. 3 is a schematic diagram in three dimensions, showing the optical layout of the system including a viewing region and one of two detecting locations.

The geometry of the optical arrangement is shown in FIG. 3, where laser beams 28 and 30 cooperate to define a beam plane 38 coincident with the plane of this figure. Each beam is separated from an axis or bisector 40 of the beams by a beam angle $\alpha$, with the full angle between beams 28 and 30 being $2\alpha$. Bisector 40 is the intersection of beam plane 38 and a plane of symmetry 42 perpendicular to the beam plane. The electric vectors of polarization of laser beams 28 and 30 are perpendicular to beam plane 38 and parallel to plane of symmetry 42, horizontal in the perspective view of FIG. 3.

As particles traverse the measuring region, they scatter the laser energy. The scattered energy is collected at a plurality of detecting locations, one of which is shown at 44 in FIG. 3. Each detecting location is defined by its linear distance from the measuring region and by two angles: an off-axis angle $\phi$, taken in plane of symmetry 42 between bisector 40 and a line 46 projected radially from the viewing region and in the plane of symmetry; and an elevation angle $\psi$, taken between line 46 and a radial projection 48 from the viewing region to the centroid of the receiving aperture that defines detecting location 44. Thus, the elevation angle $\psi$ is the angle of location 44 above plane of symmetry 42.

Figure 2:
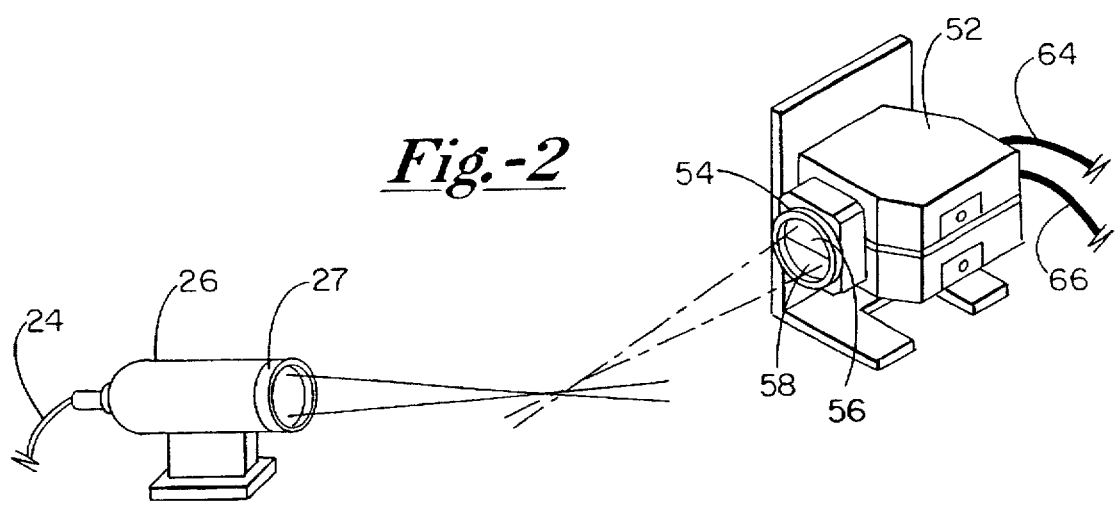
FIG. 2 is a partial view of the system in FIG. 1, further showing illumination and energy detecting components.

FIG. 2 illustrates how the equipment is positioned and adjusted to determine the geometry just explained in connection with FIG. 3. The angle $\alpha$ is determined by the focal length of lens 27 in transmitting device 26. Accordingly, a lens having a different focal length is substituted to change the beam angle. The off-axis angle $\phi$ is determined by the position and orientation of an optical receiving assembly 52. The elevation angle $\psi$ is determined by the location and masking of a receiving lens 54 of the receiving assembly. Lens 54 is centered on the plane of symmetry, to provide semicircular apertures 56 and 58 respectively above and below that plane. With respect to each aperture, the extent of masking vertically away from the plane of symmetry determines the elevation angle.

Figure 4:
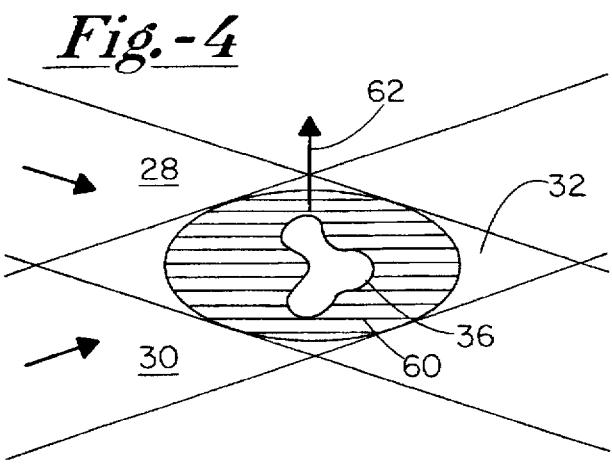
FIG. 4 is an enlarged view of the viewing region.

As can be appreciated from FIG. 4, measuring region 32 is a substantially ellipsoidal volume defined by the intersection of laser beams 28 and 30. The beam angle $\alpha$ is exaggerated, to more clearly show a series of interference fringes 60 formed throughout the measuring region and parallel to the plane of symmetry. As a particle 36 moves through the measuring volume, the scattered coherent energy fluctuates according to the alternatively light and dark fringes, in a cyclical pattern that provides a velocity vector 62 perpendicular to the plane of symmetry. Vector 62 represents either the full particle velocity or a vertical velocity component, depending upon the actual direction of travel.

A particle velocity component u is obtained from the signal frequency f, based on the equation:

$$f = f_s + u/d_f \qquad (1)$$

where $f_s$ is the shift frequency and $d_f$ is the fringe spacing. The velocity component u is positive for particle motion opposite to the direction of fringe motion, and vice versa. For a coherent energy wavelength of $\lambda$ and a beam angle $\alpha$, the fringe spacing is found using the equation:

$$d_f = \lambda/2 \sin \alpha \qquad (2)$$

With laser beams 28 and 30 generated at the same frequency, interference fringes 60 are stationary, and determine the velocity component but not its direction. Beam conditioning optics 22 can include a Bragg cell or other frequency modulator, to alter the frequency of one of the beams so that it differs from the other beam's frequency by a selected amount, e.g. 40 MHZ. Such modulation generates movement of interference fringes 60 in the vertical direction at a velocity much higher (e.g. by several orders of magnitude) than expected particle velocities. Depending on its direction of travel through the measuring region, each particle produces fluctuations in scattered energy detected as a velocity either slightly greater or slightly less than the fringe velocity. If a particle moves against the motion of the fringes, its scattered energy fluctuates at a frequency higher than the shift frequency (e.g. 40 MHZ), and vice versa. Hence, the direction of the measured velocity component is determined, based on whether a signal frequency is higher or lower than the shift frequency. For a further explanation, refer to the aforementioned U.S. Pat. No. 5,432,605.

Returning to FIG. 1, optical receiving assembly 52 collects light scattered by the particle and generates an optical output based on the received light. Due to the masking discussed above, apertures 56 and 58 are spaced apart from one another sufficiently to define two separate locations for receiving scattered energy. These locations are separated from the measuring region by about the same radial distance and are angularly spaced apart from symmetry plane 42, in opposite directions and preferably (though not necessarily) by the same elevation angle $\psi$.

The lens providing the semi-circular apertures 56 and 58 collimates the received energy. The receiving assembly has a further lens (not shown) that focuses the received energy at respective focal areas corresponding to apertures 56 and 58, for respective coupling to fiber optic cables 64 and 66.

Cables 64 and 66 provide their respective optical signals to detection electronics 68. The detection electronics include avalanche photo diodes (not shown) for converting the optical signals into respective electrical signals, and further processing circuitry (e.g. mixers, high-pass filters and low-pass filters) for generating sinusoidal electrical analogue signals as outputs on respective electrical conductors 70 and 72.

Figure 5:
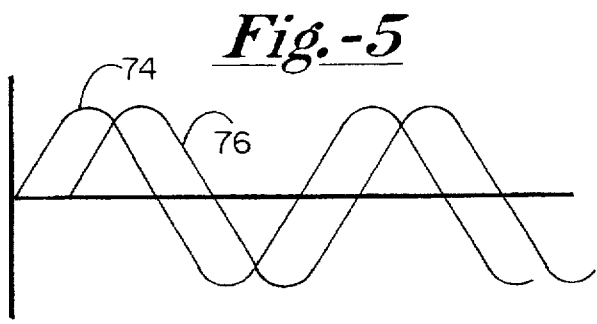
FIG. 5 is a timing diagram of signals generated by detectors of the system.
Figure 6:
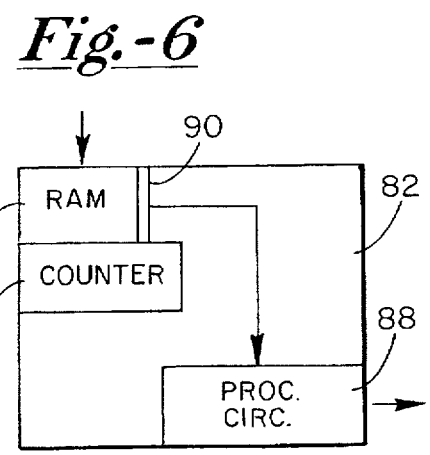
FIG. 6 is a more detailed view of a phase processor of the system.

The electrical signals, taken at points A and B on the conductors, are illustrated in FIG. 5, where the horizontal axis represents time and the vertical represents voltage or the power of scattered energy of the receiving assembly output. Signals 74 and 76, corresponding to apertures 56 and 58 respectively, have the same frequency but are shifted in phase. The phase shift is represented by the horizontal displacement of signal 76 relative to signal 74. For more detailed information regarding the detection electronics, reference is made to U.S. Pat. No. 5,432,605.

The respective analog electrical signals are provided to a signal processor 78, which converts the signals to digital information and processes this information to determine the signal frequency, the phase shift, the residence time of particle 36 within measuring region 32, and the interval between the current pair of signals and the previous pair of signals corresponding to the previous particle's traverse of the measuring region.

In connection with each data point or traverse of a particle through the measuring region, the aforementioned frequency, residence time and interval are transmitted from signal processor 78 to a computer 80. The computer is programmed to determine the velocity component parallel to fringe movement based on equations (1) and (2) above. The signals corresponding to conductors 70 and 72 exhibit the same frequency and can be checked for redundancy if desired.

The computer includes a phase processor 82 having a random access memory (RAM) 84, a counter 86 and programmable processing logic 88. RAM 84 includes multiple registers for storing multiple phase values, each representing a phase shift corresponding to a particle traverse through measuring region 32. Counter 86 is incremented each time a phase value is provided to phase processor 82, and is programmed to accumulate a count to a predetermined threshold, preferably 100 or more. Accordingly, memory 84 accumulates an ensemble or set of at least 100 phase values.

When the count in counter 86 reaches the predetermined threshold, the counter triggers RAM 84 to provide the phase values stored in the memory to processing logic 88, and logic 88 performs operations on the phase values to generate phase information. The operations preferably are performed in a software or programmed mode, e.g. with processing logic 88 configured as an erasable programmable read only memory (EPROM). However, the processing logic circuit could be hard wired as well. Primarily, the operations involve organizing the phase values into multiple phase value subsets, each with a predetermined range, thereby to generate the phase values in the form of a frequency distribution. The output of the processing circuit can comprise a histogram that portrays a complete frequency distribution of the phase values. Alternatively, the phase information can consist of a mean phase value and a standard deviation of the phase values, based on the frequency distribution.

In either event, phase processor 82 converts the phase information to particle size information, more particularly a frequency distribution or probability density function that shows how frequently a particular particle size is encountered in the flow, based on the phase information generated as a result of that flow. The particle "size" may represent a physical property such as volume, or it may represent electrical resistivity as measured in a resistivity counter.

The operations of phase processor 82 can include segmenting of the phase values based on particle velocities. To this end, RAM 84 includes a sort capability and registers, indicated at 90, for sorting and separately storing phase values based on signal frequency, i.e. particle velocity. To ensure that each particle velocity range subset includes a sufficient number of the phase values, counter 86 can be set to a substantially higher threshold, e.g. 1,000 traverses through the measuring region. Memory 84 then receives a velocity reading corresponding to each phase value. Phase processor 82 thus organizes the phase values within their appropriate velocity sets. In this event, the phase information comprises several frequency distributions (or several sets of median phase value and standard deviation), corresponding to respective velocity sets.

A salient feature of the present invention is the accumulation of phase values and arrangement of the phase values into a measured phase histogram or other ensemble for providing information on particle size.

Underlying this approach is the discovery that irregular particles measured in system 16 exhibit a surprising degree of order and simplicity in their stochastic response.

Spherical particles provide reliable individual phase measurements. Phase histograms based on multiple measurements of spherical particles are constant, in the sense that the phase histogram width does not change as the size of monodispersed particles increases, except due to changes in phase measurement accuracy as signal quality changes with changing particle diameter. The mean value of the phase histogram does increase with particle size.

Phase histograms based on multiple measurements of irregular particles are broader than corresponding phase histograms based on spherical particles. In other words, the standard deviations of the phase histograms are larger because of the irregularity of the particles involved. This broadening, or increase in standard deviation can be used as a shape factor to indicate particle irregularity.

A collection of multiple monosize stochastic particle measurements can be generated either by measuring multiple stochastic particles, or by measuring a single stochastic particle at multiple different orientations. In either event, the measurements generate a particular phase value with a certain probability. The associated probability density function is referred to herein as a monosize phase distribution (MPD) function.

In the case of a collection of particles to be measured, the probability of the occurrence of particles with a certain size D, p(D), is unknown. However, the product of the unknown probability p(D) and the MPD for size D and phase value $\Phi$, represents the joint probability of particles of size D generating a phase $\Phi$. Integrating this joint probability over a range of sizes, yields a net probability P($\Phi$) of measuring a phase shift $\Phi$ over the given size range.

In system 16, phase measurements are accumulated to yield P($\Phi$). Then, phase processor 82 is used to generate an inversion of measured phase values corresponding to a set of phase values $\Phi$, to generate a corresponding range of size values p(D). To this end, the appropriate MPD function must be determined. This requires calibration of system 16 before the system can be used to measure unknown particles.

FIG. 7 is a partial view of system 16 in a calibration mode, in which a calibration device 92 is used in lieu of two phase flow 34 that coincides with the measuring region when the system is operated in the measurement mode (FIG. 1). Calibration device 92 suspends or mobilizes particles (or a single particle repeatedly) of a known size or size distribution. System 16 is operated in the same manner during the calibration mode and measurement mode, except that in the calibration mode, known values of mean diameter $\overline{D}$ and standard deviation of the diameter $\sigma_D$ are provided to phase processor 82. The known values are compared with the resulting phase distribution P($\Phi$) to calibrate the device, more particularly to determine the characteristics of the MPD function.

There are several alternatives for calibration device 92. The most direct approach is to generate a two-phase flow, using a sample of multiple irregular particles having a known size distribution.

Alternatively, a single irregular particle can be moved in multiple traverses across the measuring region, using an electrodynamic balance 94 shown in FIG. 8 as the calibration device. This device includes a pair of disk shaped electrodes 96 and 98, and a pair or ring electrodes 100 and 102. A constant voltage $V_{DC}$ is applied between the disk electrodes to counteract a downward gravitational force on a particle 104. An oscillating voltage $V_{AC}$ is applied between the ring electrodes, destabilizing the particle so that it experiences small displacements and multiple changes in its orientation.

Accordingly, the particle generates multiple different phase shift values to provide an ensemble or set of such values. The resulting monosize phase distribution (MPD) function is a histogram of the phase values.

FIG. 9 illustrates a fluidized-bed generator 106, used to calibrate system 16 based on multiple particles of a known size distribution. The calibration sample is provided to a reservoir 108, where the particles encounter a continuous bead chain 110 and are carried to a vertical chamber, where the particles are mixed with bronze beads to prevent their agglomeration. An upward air flow carries the particles upward, leaving the heavier bronze beads behind.

Yet another alternative for calibration device 92 is a vibrating orifice drop generator 112, shown in FIG. 10. Generator 112 pumps a liquid through an orifice 114 to produce a cylindrical liquid jet 116. By vibrating orifice 114 at a fixed frequency, the liquid jet is broken into droplets 117 that are highly monodisperse, i.e. having diameters that agree within a fraction of a percent. The vibrating orifice generator is particularly well suited to calibrations for the study of non-homogeneous liquids.

When multiple particles of the same size D are measured, or when the same particle is measured repeatedly, the resulting phase distribution function q (D,$\Phi$) represents the broadening of the phase $\Phi$ for given size D, as noted above. The function q, i.e. the monosize phase distribution (MPD) function, is narrow for small particles and becomes broader with increasing particle size. The MPD relates the size distribution function p(D) to the phase distribution function P($\Phi$) as follows:

$$P(\Phi) = \int_{D_{min}}^{D_{max}} q(D, \Phi) p(D) dD \tag{3}$$

The functions p and q are assumed to satisfy the normalization condition. That is, when they are integrated over the entire ranges of D and $\Phi$, they yield a net result of 1. Thus, the function P also satisfies the normalization condition and can be expressed as:

$$\overline{\Phi} = \int_{-\Phi_0}^{360 - \Phi_0} \Phi P(\Phi) d\Phi \tag{4}$$

where integration is performed over 360°, beginning at an arbitrary value $-\Phi_0$. Substituting equation (3) into equation (4) yields:

$$\overline{\Phi} = \int_{D_{min}}^{D_{max}} \overline{\Phi}_D(D) p(D) dD, \tag{5}$$

where $$\overline{\Phi}_D(D) = \int_{-\Phi_0}^{360-\Phi_0} \Phi q(D, \Phi) d\Phi \quad (6)$$

Equation (6) represents the mean phase for the particles of a given size D.

The mean-square phase for a size distribution may be expressed as:

$$\overline{\Phi^2} = \int_{D_{min}}^{D_{max}} \overline{(\Phi^2)}_D p(D) dD, \quad (7)$$

where $$\overline{(\Phi^2)}_D = \int_{-\Phi_0}^{360-\Phi_0} \Phi^2 q(D, \Phi) d\Phi. \quad (8)$$

It has been found that in the case of transparent crystalline particles, the mean phase and the standard deviation of phase are linearly related to the corresponding particle size. This relationship is represented in the following equations for two phase factors, i.e. constant values a and b in terms of degree per micron:

$$\overline{\Phi}_D = aD, \quad (9)$$

$$\sigma_\Phi = bD, \quad (10)$$

Based on equations (9) and (10), $$[\overline{\Phi^2}]_D = \sigma_\Phi^2 + \overline{\Phi}_D^2 = (a^2+b^2)D^2 = (saD)^2, \quad (11)$$

where the value s is a shape factor or inhomogeneity factor related to phase factors a and b as follows:

$$s = \sqrt{1 + \left(\frac{b}{a}\right)^2} \quad (12)$$

Ideally, s is equal to 1 for spherical particles and increases above 1 with increasing particle irregularity. Substituting equations (9) and (11) into equation (5) yields:

$$\overline{\Phi} = a \int_{D_{min}}^{D_{max}} Dp(D) dD = a\overline{D}, \text{ or } \overline{D} = \frac{\overline{\Phi}}{a}, \quad (13)$$

Substituting equations (9) and (11) into equation (7) yields:

$$\overline{\Phi^2} = a^2 s^2 \int_{D_{min}}^{D_{max}} D^2 p(D) dD = a^2 s^2 \overline{D^2}. \quad (14)$$

The standard deviation of the particle size, $\sigma_D$, may be expressed as:

$$\sigma_D = \sqrt{\overline{D^2} - \overline{D}^2} = \frac{1}{a} \sqrt{\frac{\overline{\Phi^2}}{s^2} - \overline{\Phi}^2}. \quad (15)$$

Equations (13) and (14) show that the first two moments of the size distribution are related directly to the first two moments of the phase distribution, provided that the mean and standard deviation of the monosize phase distribution function vary linearly with size. This enables measurement of the mean and standard deviation of the particles, without a priori knowledge of the shape of the size distribution function.

In general, if the first few moments of the MPD can be expressed as polynomials in particle size. If the order of the polynomial does not increase with the order of the moment, then the lower order moments of the phase distribution can be translated into corresponding lower-order moments of the size distribution.

The use of equations (13) and (15) to measure the mean and standard deviation of particle size, requires calibration to determine the values a and s. Of course, b becomes known as well, based on equation (12). In the calibration mode, phase processor 82 receives the mean size $\overline{D}$ and standard deviation $\sigma_D$ and evaluates a, b and s based on the detected phase values $\Phi$.

In the measurement mode, values for a, b and s already stored are used by the phase processor to determine the particle size distribution p(D).

Reconstruction of a size distribution p(D) (based on a phase distribution $P(\Phi)$ and the quantities a, b, and s) is enhanced by knowing the nature of the monosize phase distribution function. Given equations (9) and (10) above, a Gaussian model of the MPD function using the values a and b is expressed as:

$$q(D, \Phi) = \frac{1}{\sqrt{2\pi} \, bD} \exp\left[-\frac{1}{2}\left(\frac{\Phi - aD}{bD}\right)^2\right]. \quad (16)$$

Alternatively, parameters a and b can be used to express the MPD function as a Laplace or a double exponential distribution, as follows:

$$q(D, \Phi) = \frac{1}{\sqrt{2bD}} \exp\left[-\sqrt{2}\left|\frac{\Phi - aD}{bD}\right|\right]. \quad (17)$$

Once the MPD function is established, a variety of numerical methods may be used for inverting equation (3) above to determine a size distribution function based on a given phase distribution function.

For example, considering n different values of phase $\Phi_i$, and n values of particle size $D_j$, equation (3) above may be expressed as a set of algebraic equations:

$$P_1 = (q_{11}p_1 + q_{12}p_2 + \ldots + q_{1n}p_n)\Delta D \quad (18)$$
$$P_2 = (q_{21}p_1 + q_{22}p_2 + \ldots + q_{2n}p_n)\Delta D$$
$$\vdots$$
$$P_n = (q_{n1}p_1 + q_{n2}p_2 + \ldots + q_{nn}p_n)\Delta D$$

Where $P_i = P(\Phi_i)$, $p_j = p(D_j)$ and $q_{ij} = q(D_j, \Phi_i)$. This approach replaces the integral in equation (3) with a summation and values of $D_j$ separated by an interval $\Delta D$. Hence, there are n linear algebraic equations provided for n unknowns, i.e. the values $p_1, p_2 \ldots p_n$.

The algebraic equations (18) can be written in vector notation, as:

$$\vec{P} = [Q]\vec{p}\Delta D, \quad (19)$$

where $\vec{P}$ and $\vec{p}$ are vectors with n elements of P and p respectively. The matrix [Q] is given as $$[Q] = \begin{bmatrix} q_{11} & q_{12} & \cdots & q_{1n} \\ q_{21} & q_{22} & \cdots & q_{2n} \\ \cdot & \cdot & & \cdot \\ \cdot & \cdot & & \cdot \\ \cdot & \cdot & & \cdot \\ q_{n1} & q_{n2} & \cdots & q_{nn} \end{bmatrix} \quad (20)$$

Finally, solving equation (19) requires the inverse of the matrix [Q], to find the vector $\vec{p}$ concerning the size distribution based on measured phase values, as follows:

$$\vec{p} = \frac{[Q]^{-1}\vec{P}}{\Delta D} \quad (21)$$

Whether programmed or hard wired, phase processor 82 (more particularly logic 88) is configured to invert the matrix [Q] employing standard mathematical techniques. These techniques are based on a description of the monosize phase distribution (MPD) function, e.g. using the Gaussian or Laplace models noted above.

Alternatively, a neural network within logic 88 enables an inversion of equation (3) with no need to model or otherwise describe the MPD function. Given a sufficient amount of data (size inputs and phase inputs) to the neural network during calibration, the network provides a mapping from a multidimensional continuous input space (phase information) to a multidimensional continuous output space (size information) when in the operating mode. The first and last layers of the network represent the input and output, respectively. Placing all required processors on a single integrated circuit chip enhances efficiency of the neural network.

FIGS. 11 and 12 schematically illustrate, in simplified form, a neural network used as a means for converting phase distributions into size distributions without generating a monosize phase distribution function. In FIG. 11, a neural network 118 is shown in a training mode, where a phase distribution function P and a size distribution function p, both known, are input to the network. For the purpose of illustration, phase distribution function P is represented by three discrete values $\Phi_1$, $\Phi_2$ and $\Phi_3$. Likewise, the size distribution p is represented by diameters $D_1$, $D_2$ and $D_3$. In practice, both of the distributions would be represented by many more values, e.g. in the range of 50–100. As the phase values and size values are provided to the network, weight functions $w_{11}$, $w_{12}$, etc. are produced within a layer A of the network. In actual practice, the network would include several further layers, with further weight functions W provided for generating values $B_1$, $B_2$, etc. based on inputs of $A_1$, $A_2$, etc. The weight functions W are produced to generate values $A_1$ according to the function:

$$f(W_{11}P(\Phi_1)+W_{21}P(\Phi_2)+W_{31}P(\Phi_3))$$

with similar expressions for finding $A_2$ and $A_3$. More data provided in the training mode lead to more reliable values of weight functions W.

In FIG. 12, which illustrates the operating mode, measured phase distributions P are input to the network, which calculates the corresponding size distributions p.

Experiments using system 16 have confirmed the utility of generating phase distribution functions based on multiple phase values to determine corresponding size distribution functions. Further, the experiments have enabled identification of parameters that influence phase values, and have demonstrated a high reliability of the double exponential function in modeling the MPD function.

In the experiments, laser head 18 was an argon-ion laser used to generate a laser beam having a wavelength of 0.5145 microns. While the wavelength remained unchanged throughout the experiments, other parameters including fringe spacing, off-axis angle, and elevation angle, were changed.

Fringe spacing was controlled by using different transmitting lenses 27 having focal lengths of 310 mm and 500 mm respectively, while maintaining a spacing of 17 mm between laser beams 28 and 30. The shorter focal length lens sets a beam angle $\alpha$ of 1.57°, corresponding to a fringe spacing of 9.4 microns. The longer focal length lens set a beam angle of 0.97°, with the corresponding fringe spacing 15.1 microns.

Optical receiving assembly 52 was positioned angularly to provide alternative off-axis angles of 45° and 90°.

Finally, the aperture height of semicircular apertures 56 and 58 was set alternatively at aperture heights of 7 mm, 15 mm and 35 mm, to provide corresponding elevation angle settings of 0.87°, 1.62° and 2.93°.

These parameter settings are summarized in Table 1 below, which also incorporates sensitivity values calculated based on pure refraction by spherical particles, using a refractive index of 1.76 for aluminum oxide.

The aluminum oxide particles tested were provided with a volume distribution of particle size available from the supplier, Norton Company of Worcester, Mass. The information is available in the form of a cumulative histogram measured by a Coulter counter, i.e. an electrical resistivity counter, which measures individual particles by volume. The corresponding particle sizes are expressed as diameters of "equivalent spheres".

TABLE 1

| Aperture height (mm) | Elevation angle (degrees) | Sensitivity for spherical particles, degrees/μm | | |
|---|---|---|---|---|
| | | $\phi = 45°$, $d_f = 9.4$ μm | $\phi = 45°$, $d_f = 15.1$ μm | $\phi = 90°$, $d_f = 15.1$ μm |
| 35 | 2.93 | 2.03 | 1.26 | 1.19 |
| 15 | 1.62 | 1.125 | 0.698 | 0.661 |
| 7 | 0.87 | 0.604 | 0.375 | 0.355 |

The cumulative distribution, converted into a probability density function, is shown in FIG. 13 as curve 120. This curve represents the volume of the particulate matter as a function of size D. Because larger particles encompass more volume, this distribution is biased towards larger diameters. Accordingly, curve 122 in FIG. 7 represents the same particle size distribution as a number distribution rather than a volume distribution, more accurately representing the size distribution function p(D). Curves 120 and 122 appear to fit a Gaussian distribution satisfactorily.

The aluminum oxide particles tested were fluidized using compressed air, with phase measurements thus based on a two-phase flow consisting of air and the particles.

FIGS. 14–16 show histograms of measured phase values generated under various operating conditions. In these figures, phase values are represented on the basis that refracting spherical particles yield positive phase values, while reflecting particles yield negative phase values. Aluminum oxide particles, if spherical, would be predominantly refracting. However, measured phase histograms for the irregular aluminum oxide particles tested, exhibited discontinuities at 0°/360° when phase shifts were assumed to be positive. Meaningful, continuous histograms, as represented in FIGS. 14–16, were obtained by assuming that phase shifts in excess of 270° actually were negative, and interpreting them as "Φ-360°", where Φ is the value actually measured. In other words, the value $\Phi_0$ as used in equation (4) is 90°, calling for integration over a range from negative 90° to 270°.

In FIG. 14, curve 124 represents a phase distribution based on a fringe spacing of about 15.1 microns (α=0.97°), while curve 126 reflects a fringe spacing of about 9.4 microns. In both cases, the off-axis angle is 45° and the aperture height is 7 mm.

Comparison of curves 124 and 126 discloses a dependency of phase values upon fringe spacing. In particular, the mean phase value $\overline{\Phi}$ is 33.7° for a fringe spacing of 15.1 microns. For the finer fringe spacing of 9.4 microns, the mean phase value is 53.4°. Hence, the mean phase appears to vary linearly with the ratio of mean particle size to fringe spacing, i.e. $\overline{D}/d_f$. The full-width-half-maximum values of curves 124 and 126 appear to follow the same linear trend, being 50° and 80° for curves 124 and 126, respectively. This supports an inference that the standard deviation of phase, σ, also varies linearly with $\overline{D}/d_f$. One further can infer that the linear relationship holds not only for a varying fringe spacing and a constant mean particle size as shown, but also when the particle size is varied while maintaining a constant fringe spacing—provided that particle sizes remain within the practical range discussed above, i.e. less than about four times the fringe spacing, yet large enough to generate a measurable phase difference.

Based on the sensitivity values in Table 1 and the mean phase values for curves 124 and 126, the mean particle diameter (for particles assumed to be spherical) would be about 90 microns, much more than the actual mean of 26.9 microns. This demonstrates the considerable error that would arise from an assumption that these irregular particles can be represented by "equivalent spheres".

In FIG. 15, curves 128, 130 and 132 are based on respective aperture heights of 7 mm, 15 mm and 35 mm, corresponding to respective elevation angles of 0.87°, 1.62° and 2.93°. In these cases the off-axis angle is 90° and the fringe spacing is 15.1 microns.

The progression from curve 128 to curve 132 represents a change of elevation angle by a factor larger than three. There is a corresponding change in the mean phase value, but by less than 18%. Likewise the width of the distribution increased, but only by about 30%.

Given the sensitivity factors in Table 1, tripling the elevation angle is expected to produce a similar increase (i.e. tripling) in the mean phase value in the case of spherical particles. Thus, data in FIG. 15 demonstrate that irregular particles are considerably less sensitive to changes in the elevation angle, which alleviates the need for a strict tolerance in setting the elevation angle when measuring irregular particles.

In FIG. 16, curves 134 and 136 are based on off-axis angles of 45° and 90°, respectively. Fringe spacing is maintained at 15.1 microns and aperture height is maintained at 7 mm.

Curves 134 and 136 show that as the off-axis angle increases from 45° to 90°, the mean phase value increases from 32.5° to 33.7°. The variance is small and similar to that expected in the case of spherical particles. However, the increase in off-axis angle reduces the standard deviation of the distribution from 41.4° to 28.5°.

As discussed above, system 16 can be calibrated with phase factors a and b, or alternatively with factor a and shape factor s for reconstructing size distribution functions based on phase distribution functions, given sufficient knowledge of the monosize phase distribution function. For the size distribution in FIG. 13 and the corresponding phase distribution in FIG. 14 (15.1 micron fringe spacing), the value of phase factor a is 1.255 degrees/micron, and the value of shape factor s is 1.49. The value of phase factor b is 1.39 degrees/micron.

When the values of factors a and b are applied to the Gaussian model of the MPD function, the resulting modeled function, within a particle size range of two standard deviations on either side of the mean size (i.e. D±2σ or 20.9–36.3 microns), yields peak values between 0.83 percent/degree and 1.51 percent/degree. These peak values are much smaller than the peak values of curve 124 in FIG. 14.

By contrast, when the values of size factors a and b are applied to the Laplace (double exponential) model, the modeled function is a much closer match to the function based on measured phase values.

The Laplace distribution as a model is tested by computing the phase distribution, again for the case of 15.1 micron fringe spacing, i.e. curve 124 in FIG. 14. Equation (17) above is substituted into equation (3), to yield:

$$P(\Phi) = \int_{D_{min}}^{D_{max}} \frac{1}{\sqrt{2}bD} \exp\left[-\sqrt{2}\left|\frac{\Phi - aD}{bD}\right|\right] p(D) dD. \quad (22)$$

The above integral is evaluated over a range of phases from negative 90° to 270°, again using 1.255 degrees/micron and 1.39 degrees/micron as the respective values of parameters a and b. The number distribution (curve 122 in FIG. 13) is again used as the size distribution function p(D).

In FIG. 17, curve 138 represents the integration of equation (23) over a range of from three standard deviations less than the mean size, to three standard deviations above the mean size, i.e. 15.08 microns to 38.72 microns. Integration was performed by Simpson quaditure using 100 intervals.

Curve 140 in FIG. 17 is the same as curve 124 in FIG. 14 and represents the distribution of measured phase values for the case of 15.1 micron fringe spacing. Curves 138 and 140 show reasonable agreement between the measured data and the simulation, particularly as to the flatness factors and peaks of the distributions. There is some skew (horizontal offset) between the two distributions, which might be eliminated by employing an asymmetric exponential distribution as the model for the MPD function.

FIG. 18 schematically illustrates an alternative particle measuring system 142 including a laser source 144 for generating collimated laser beams 146 and 148 that interfere with one another at their intersection to form a measuring region 150. A two-phase flow of particles in air is directed across the measuring region.

Light scattered by the particles is sensed at three detectors 152, 154 and 156. The detectors provide their electrical signal outputs to detection electronics, signal processing circuitry and phase processing circuitry, not shown but similar to that in FIG. 1. Consequently, each traverse of a particle cross measuring region 150 generates two phase values (i.e. phase differences), rather than one. The pairs of phase values can be used to determine particle characteristics beyond size, e.g. index of refraction and temperature. For a more detailed explanation of how phase values are employed in this manner, reference is made to U.S. Pat. No. 5,453,837 (Naqwi et al assigned to the assignee of this application).

FIG. 19 discloses a further alternative particle measuring system 158 including two transmitting optics modules 160 and 162 for generating respective pairs of interfering laser beams 164 and 166. Beam pairs 164 and 166 form respective measuring regions that overlap one another at 168, so that a two-phase flow carries particles through both measuring regions simultaneously. The bisecting axes of beam pairs 164 and 166 are perpendicular to one another and define a beam plane.

Several optical receivers 170, 172 and 174 are positioned in the beam plane to receive light scattered by particles traversing the measuring regions. At least one of the optical receivers is configured to receive energy from both beam pairs 164 and 166, employing electronic or optical filtering to distinguish between the beam pairs. The manner of distinguishing is further explained in the aforementioned U.S. Pat. No. 5,432,605, in connection with FIG. 9 of that patent.

As an alternative, an additional optical receiver can be provided, in which case all receivers can be dedicated to a particular beam pair. In any event, the detector outputs are provided to signal and phase processing circuitry as previously described.

System 158 enhances the characterization of irregular particles, since each particle provides two indications of size, taken from different directions, as it traverses the measuring regions. This facilitates size measurement, enabling the user to generate two different phase distribution functions corresponding to the different viewing directions, or a composite phase distribution function composed of multiple composite phase values, each composite value based on a pair of measured phase values.

If desired, a third transmitting optics module 176 can be positioned to generate a pair of laser beams that form a third measuring region that overlaps the other two at 168. This permits generation of phase measurements based on viewing the particle from three mutually perpendicular directions.

FIG. 20 is a schematic view of a further alternative particle measuring system 178 for characterizing particles 180 supported on a solid medium 182. A transmitting optics module 184 generates a pair of laser beams 186 that interfere with one another at a measuring region 188 coincident with an upper surface of the solid medium.

As the medium is moved horizontally, particles embedded or otherwise supported in the medium traverse the measuring region and scatter light, primarily by reflection. Detectors 190 and 192 are positioned to receive the reflected energy, and provide their respective outputs to signal and phase processing circuitry as previously described.

Thus in accordance with the present invention, stochastic particles or other light scattering elements are caused to traverse a measuring region formed by two interfering laser energy beams. Each individual traverse scatters light that is detected to provide a phase measurement. Accumulated phase values, based on multiple traverses, are used to create histograms or probability density functions that represent sizes or other characteristics of the light scattering elements.

Accordingly, reliable information is obtained, despite the fact that the light scattering elements, taken individually, exhibit unpredictable light scattering tendencies that vary with their orientation. The result is a highly reliable characterization of multiple particles or other elements, despite their irregularities in shape, composition, or both. Further according to this invention, particles of a known size distribution, or a single particle of a known size measured repeatedly, is used to calibrate a particle measuring device. Calibration can involve either storing a complete conversion function for generating a size distribution based on a phase distribution, or can involve merely storing key size and shape factors applied to a Gaussian or a double exponential function, to generate a monosize phase distribution function.

What is claimed is:

1. An apparatus for non-contact measuring of stochastic light scattering elements including:

an illumination apparatus for selectively directing coherent energy onto a medium, to define a measuring region traversed individually by light scattering elements contained in the medium as the medium moves relative to the measuring region;

an energy detecting apparatus for sensing the coherent energy scattered by each of the light scattering elements as it traverses the measuring region, by sensing the scattered coherent energy at least at first and second different locations spaced apart from the measuring region and generating first and second signals based on the coherent energy sensed at the first and second locations, respectively;

a signal processor, operatively coupled to the energy detecting means to receive the first and second signals, for generating a phase value corresponding to each light scattering element, each said phase value representing a temporal shift between the first and second signals; and an information processing system including (i) a memory for receiving and accumulating multiple phase values corresponding to multiple scattering element traverses through the measuring region; (ii) sorting logic for organizing the accumulated phase values by increments of phase, to generate phase information describing a phase histogram of the accumulated phase values; and (iii) conversion logic for applying conversion information to the phase information, to generate element characterizing information describing a scattering element histogram of multiple scattering element characterizing values corresponding to the multiple scattering element traverses.

2. The apparatus of claim 1 wherein:
said phase information comprises said phase histogram.

3. The apparatus of claim 2 wherein:
said element characterizing information comprises said scattering element histogram.

4. The apparatus of claim 1 wherein:
said phase information comprises a mean value of phase and a standard deviation of phase, and the conversion information includes a conversion function for determining the element characterizing information based on the mean value of phase and the standard deviation of phase.

5. The apparatus of claim 4 wherein:
said element characterizing information comprises a mean value of light scattering element size and a standard deviation of the light scattering element size.

6. The apparatus of claim 1 wherein:
said multiple scattering element traverses consist of multiple repeated traverses of a single light scattering element through the measuring region.

7. The apparatus of claim 1 wherein:
said multiple scattering element traverses are comprised of single traverses through the measuring region by multiple, different light scattering elements.

8. The apparatus of claim 1 wherein:
the element characterizing information includes a particle irregularity indication.

9. The apparatus of claim 1 wherein:
the information processing system further includes logic for providing a velocity indication based on the frequency of the first and second signals.

10. The apparatus of claim 9 further including:

a sorting means for grouping the accumulated phase values into a plurality of sets based on velocity, each of said sets corresponding to a different velocity range.

11. The apparatus of claim 1 wherein:

the illumination apparatus includes means for generating two linearly propagating beams of coherent energy and causing the beams to interfere with one another at their intersection to define the measuring region.

12. The apparatus of claim 11 wherein:

the particle illumination means further includes a modulation means for shifting the frequency of one of the coherent energy beams by a predetermined frequency amount.

13. The apparatus of claim 1 further including:

a calibration means for generating conversion information, and providing said conversion information to the conversion logic.

14. The apparatus of claim 13 wherein:

the calibration means includes a calibration device for suspending test elements of a known size distribution, said calibration device being mounted with respect to the illumination means and the detecting means such that the test elements traverse the measuring region and scatter the coherent energy, wherein the detecting apparatus senses the scattered coherent energy to generate first and second calibration signals, and the signal processor generates a test value representing a temporal shift between the first and second calibration signals, wherein the memory receives and accumulates multiple test values corresponding to multiple test element traverses through the measuring region, and provides the multiple test values to the conversion logic; and the conversion logic retains said multiple test values as a monosize phase distribution function $q(D,\Phi)$ describing the distribution of phase values $\Phi$ for a selected particle size D; said monosize distribution function being applied to the phase information by the conversion logic to generate the element characterizing information.

15. The apparatus of claim 14 wherein:

said conversion means applies said monosize phase distribution function $q(D,\Phi)$ to a measured distribution function $P(\Phi)$ of a phase ($\Phi$), thereby to generate a size distribution function $p(D)$ as the element characterizing information according to the following equation:

$$P(\Phi) = \int_{D=Dmin}^{D=Dmax} q(D, \Phi)p(D)dD.$$

16. The apparatus of claim 1 wherein:

the conversion logic contains numerical phase factors a and b, relating the particle size D to the mean and standard deviation of a test phase distribution according to the equations:

$$\Phi_d = aD;$$

and $$\sigma_D = bD,$$

where $\Phi_d$ is the mean of the test phase distribution and $\sigma_D$ is the standard deviation of the test phase distribution; and the conversion logic applies the phase factors a and b to said phase information, to produce said element characterizing information.

17. The apparatus of claim 15 wherein:

said monosize phase distribution function is a double exponential function.

18. The apparatus of claim 15 wherein:

said calibration device comprises one of the following: a fluidized bed aerosol generator, a vibrating orifice droplet generator, and an electrodynamic balance.

19. The apparatus of claim 13 wherein:

said conversion means includes a neural network having an input stage and an output stage, means for providing a known distribution of phase values as inputs to the input stage, and means for providing corresponding known size distributions as inputs to the output stage, thereby to provide weight functions in said neural network for generating said element characterizing information at said output stage, responsive to receiving said phase information at the input stage.

20. The apparatus of claim 1 wherein:

said conversion information comprises a function relating the phase information to the element characterizing information in non-linear fashion.

21. The apparatus of claim 20 wherein:

the conversion information comprises a monosize phase distribution function $q(D,\Phi)$ describing the distribution of phase values $\Phi$ for a selected particle size D.

22. The apparatus of claim 20 wherein:

the conversion information is comprised of weight functions of a neural network within the conversion logic.

23. The apparatus of claim 1 wherein:

said energy detecting means further senses the scattered coherent energy at a third location spaced apart from the measuring region to generate a third signal and provides the third signal to the signal processing means; and wherein the signal processing means combines the first, second and third signals to generate at least two of said phase values corresponding to each of said traverses.

24. A process for characterizing irregular or inhomogeneous light scattering elements, comprising:

providing a medium containing light scattering elements;

selectively directing coherent energy onto the medium, to define within the medium a measuring region traversed by light scattering elements contained in the medium as the medium moves relative to the measuring region;

detecting the coherent energy scattered by each of the light scattering elements at two different locations spaced apart from the measuring region, and generating first and second signals based on the energy detected at the first and second locations, respectively;

combining the first and second signals to generate a phase value associated with each light scattering element traverse of the measuring region, said phase value representing a temporal shift between the first and second signals;

accumulating multiple phase values corresponding to multiple traverses through the measuring region;

sorting the accumulated multiple phase values by increments of phase, to generate phase information describing a phase histogram of the accumulated phase values; and applying conversion information to the phase information to generate element characterizing information describing a scattering element histogram of multiple scattering element characterizing values corresponding to the multiple scattering element traverses.

25. The process of claim 24 wherein:

said phase information comprises a probability density function of measured phase values $\Phi$ providing a phase distribution function $P(\Phi)$ of scattering element sizes D, said element characterizing information comprises a size distribution function $p(D)$; and wherein said conversion step comprises determining the size distribution function based on the phase distribution function and a previously stored monosize phase distribution function $g(D,\Phi)$, by inverting the equation:

$$P(\Phi) = \int_{D=D_{min}}^{D_{max}} q(D, \Phi) p(D) dD.$$

26. The process of claim 24 further including:

storing a monosize phase distribution function in a conversion device for use in performing said conversion step whereby said conversion step includes providing the phase information as an input and generating said element characterizing information as an output of the conversion device.

27. The process of claim 26 wherein:

said step of storing the monosize phase distribution function further includes illuminating a medium containing test elements of a known size distribution, detecting the coherent energy scattered by each traverse of a test element through the measuring volume to generate first and second test signals, combining the first and second test signals to generate a test value representing phase, and combining multiple test values corresponding to multiple particle traverses through the measuring region, to generate a calibration phase distribution; and storing the calibration phase distribution in the conversion device for use in converting the phase information to the measurement output.

28. The process of claim 25 further including:

generating the monosize phase distribution function based on a mean value and a standard deviation value of a known phase distribution based on a known size distribution, storing the generated monosize phase distribution function to a conversion device, and inputting the phase information to the conversion device.

29. The process of claim 28 wherein:

said monosize phase distribution function is either a double exponential function or a Gaussian function.

* * * * *

UNITED STATES PATENT AND TRADEMARK OFFICE
CERTIFICATE OF CORRECTION

PATENT NO. : 5,784,160
DATED : July 21, 1998
INVENTOR(S) : Naqwi, Amir

Page 1 of 1

It is certified that error appears in the above-identified patent and that said Letters Patent is hereby corrected as shown below:

On the cover page after "[73] Assignee:" delete "TSI Corporation" and insert -- TSI Incorporated --

Signed and Sealed this

Twelfth Day of June, 2001

*Attest:*

*Attesting Officer*

NICHOLAS P. GODICI
*Acting Director of the United States Patent and Trademark Office*